United States Patent
Noshi et al.

(10) Patent No.: US 8,094,774 B2
(45) Date of Patent: Jan. 10, 2012

(54) X-RAY COMPUTED TOMOGRAPHY APPARATUS

(75) Inventors: Yasuhiro Noshi, Otawara (JP); Satoru Nakanishi, Utsunomiya (JP); Satoshi Saito, Yaita (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 541 days.

(21) Appl. No.: 12/256,855

(22) Filed: Oct. 23, 2008

(65) Prior Publication Data

US 2009/0110139 A1  Apr. 30, 2009

(30) Foreign Application Priority Data

Oct. 25, 2007 (JP) .................................. 2007-278062

(51) Int. Cl.
*A61B 6/03* (2006.01)
(52) U.S. Cl. ......................................... 378/15; 382/131
(58) Field of Classification Search ................ 378/4, 15; 382/128–131
See application file for complete search history.

(56) References Cited

U.S. PATENT DOCUMENTS

2004/0086074 A1* 5/2004 Taguchi ............................. 378/4
2005/0094761 A1* 5/2005 Hagiwara ........................ 378/15

FOREIGN PATENT DOCUMENTS

JP  2004-113271  4/2004

* cited by examiner

*Primary Examiner* — Edward Glick
*Assistant Examiner* — John Corbett
(74) *Attorney, Agent, or Firm* — Oblon, Spivak, McClelland, Maier & Neustadt, L.L.P.

(57) ABSTRACT

A control unit performs helical scanning an subject while moving a top along a direction substantially parallel to a body axis. An acquisition unit acquires projection data via an X-ray detector. A projection data extraction unit extracts a projection data set necessary for the reconstruction of image data associated with a predetermined slice position from the projection data. A weighting unit assigns a smaller weight to first projection data of the extracted projection data than a weight assigned to second projection data, the first projection data being acquired outside a predetermined period including a predetermined acquisition time of the projection data at the predetermined slice position, the second projection data being acquired within the predetermined period. A reconstruction processing unit reconstructs image data on the basis of the first projection data and the second projection data to which the weights are assigned.

11 Claims, 10 Drawing Sheets

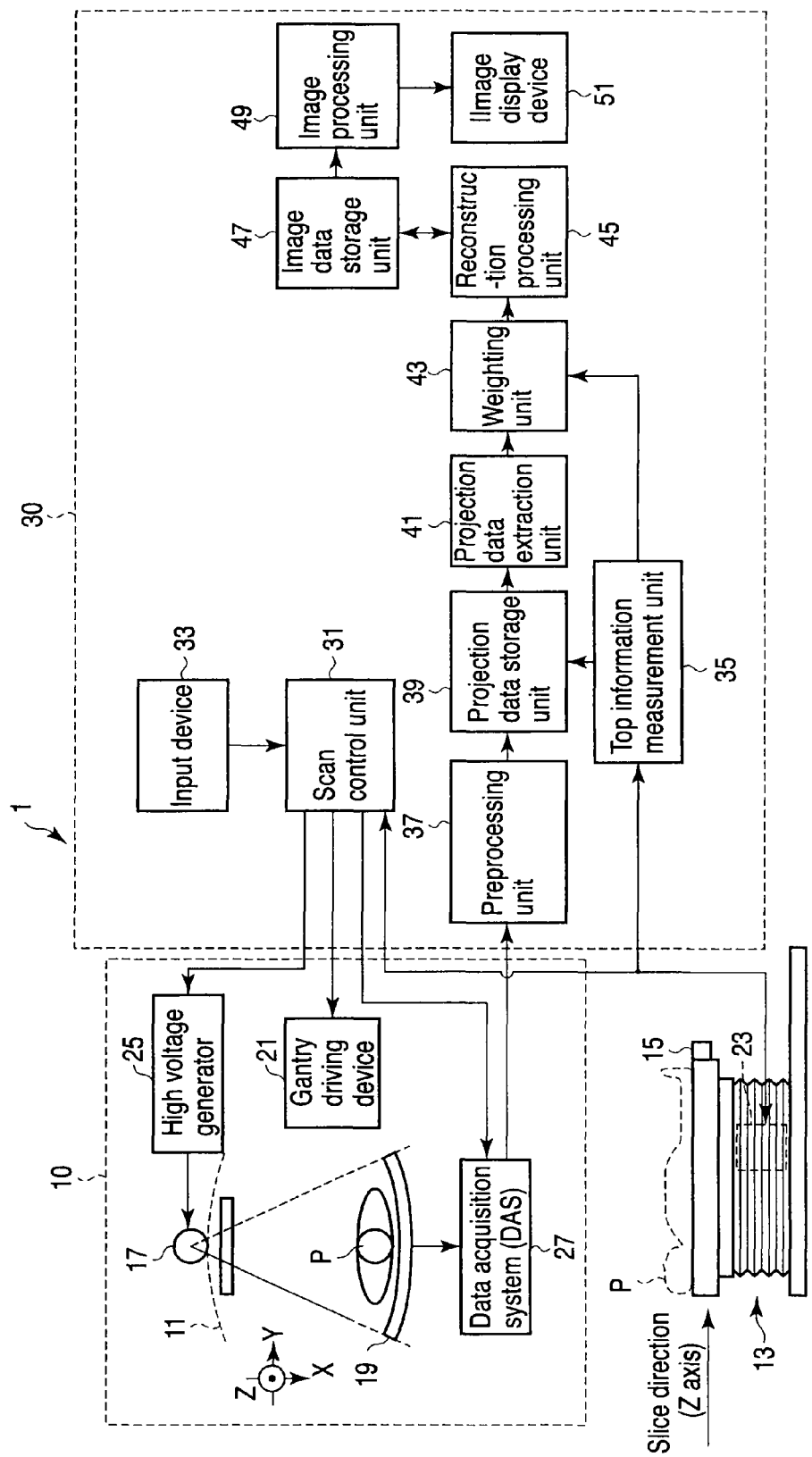
F I G. 1

Contribution table UT in constant speed helical scanning UT

Contribution table VT in variable speed helical scanning VT

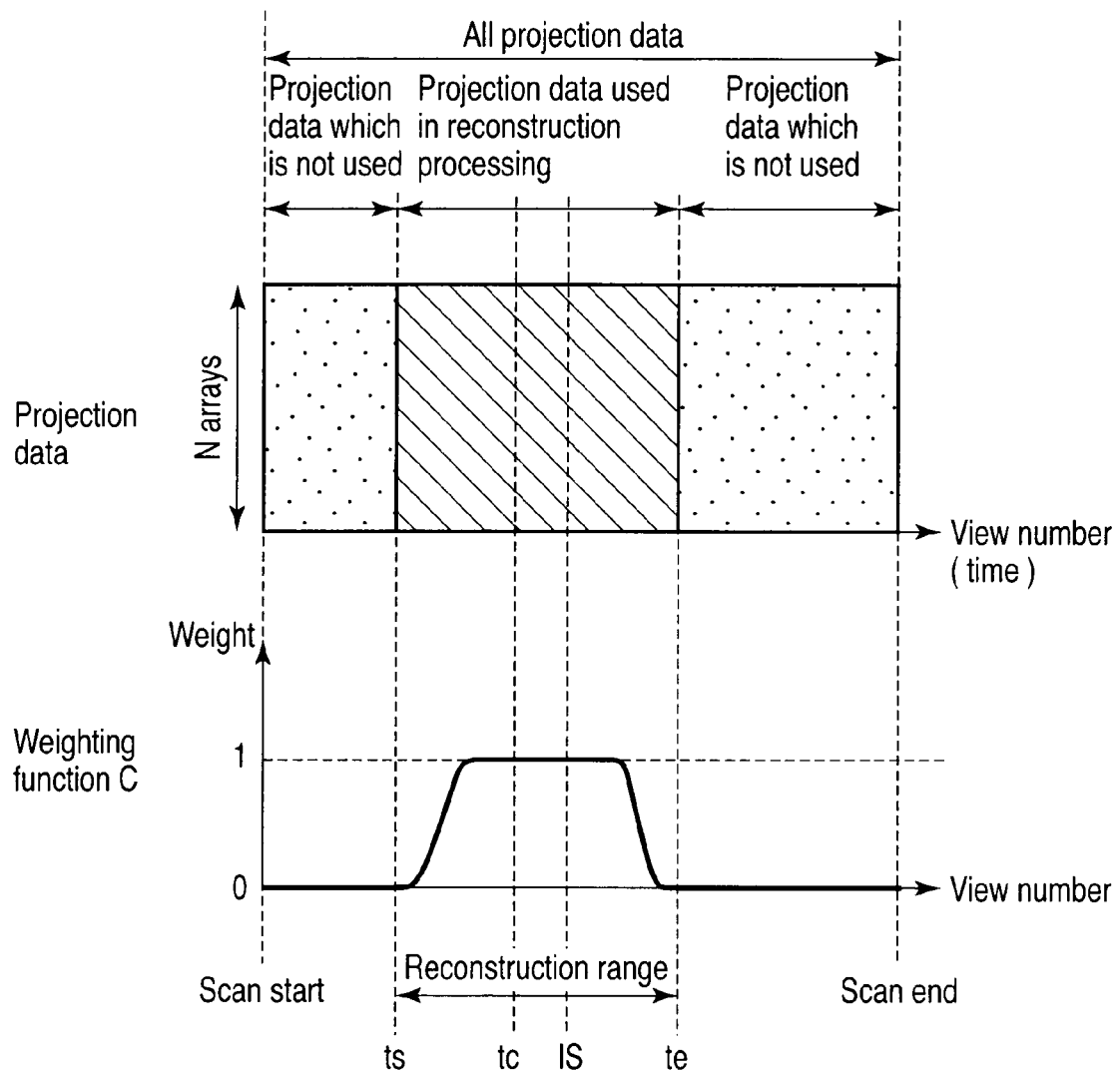
F I G. 7

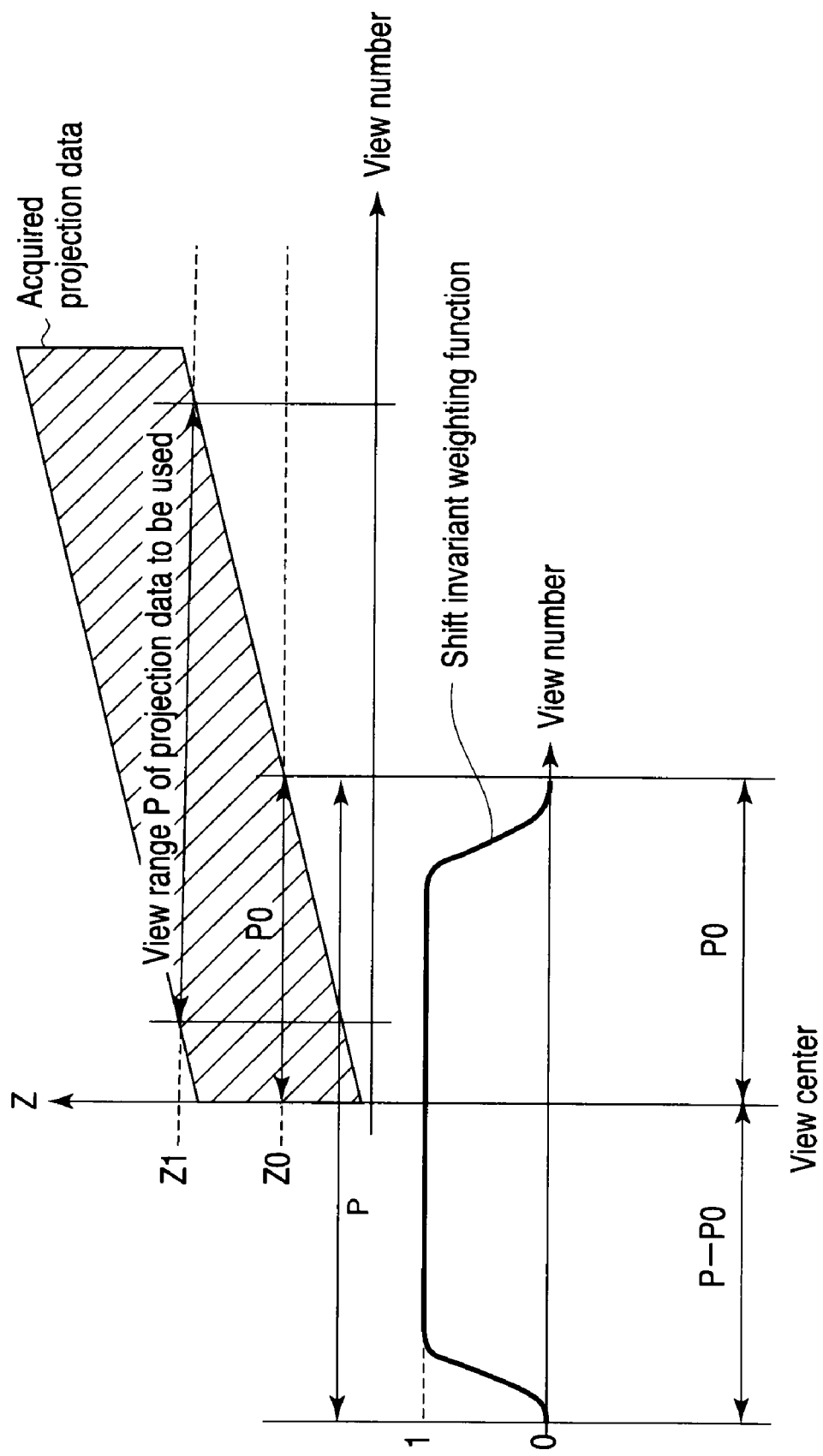
F I G. 9

X-RAY COMPUTED TOMOGRAPHY APPARATUS

CROSS-REFERENCE TO RELATED APPLICATIONS

This application is based upon and claims the benefit of priority from prior Japanese Patent Application No. 2007-278062, filed Oct. 25, 2007, the entire contents of which are incorporated herein by reference.

BACKGROUND OF THE INVENTION

1. Field of the Invention

The present invention relates to an X-ray computed tomography (CT) apparatus which performs helical scanning.

2. Description of the Related Art

Helical scanning is used to acquire projection data by scanning an subject with cone beam X-rays while moving a top on which the subject is placed. The image data based on the projection data acquired by helical scanning is reconstructed in the following general sequence:
1. extracting projection data (a projection data set) necessary for reconstruction of one image;
2. performing data redundancy correction (weighting);
3. performing filtering; and
4. performing backprojection It suffices to interchange steps 2 and 3. Consider weighting in step 2. Reconstruction processing (half scan method) uses projection data (a projection data set) in the range from $(-\pi/2-\alpha/2)$ to $(+\pi/2+\alpha/2)$, centered on a target slice position. A weighting function is designed to assign smaller weights to projection data farther from the slice position and assign larger weights to projection data closer to the slice position. When the speed of the top (helical pitch) is constant, the slice position on this weighting function matches the view center (half of the total number of views of the projection data set) of the projection data set extracted in step 1. Such a weighting function having a weight distribution symmetrical to the view center is called a shift-invariant weighting function.

As an application of helical scanning, there is available a variable speed helical scanning scheme of performing scanning while changing the speed of the top (helical pitch). FIG. 11 is a graph showing the relationship between a weighting function in variable speed helical scanning (acceleration) and the position of an X-ray tube. In a case of variable speed helical scanning (acceleration), the number of views from $(-\pi/2-\alpha/2)$ to 0 is larger than that from 0 to $(+\pi/2+\alpha/2)$. As shown in FIG. 11, therefore, when the speed of the top is changed during scanning, the slice position IS does not match a view center tc of a projection data set used for reconstruction. If the shift-invariant weighting function is applied to the variable speed helical scanning scheme in which the slice position IS does not match the view center tc, artifacts occur.

BRIEF SUMMARY OF THE INVENTION

It is an object of the present invention to reduce artifacts due to the mismatch between the position of image data to be reconstructed and the view center of projection data in an X-ray CT apparatus which reconstructs image data on the basis of the data obtained by helically scanning an subject.

An X-ray CT apparatus according to a first aspect of the present invention comprises: an X-ray tube configured to generates X-rays; an X-ray detector configured to detects X-rays generated from the X-ray tube and transmitted through an subject placed on a top; a support unit configured to rotatably supports the X-ray tube and the X-ray detector; a bed configured to includes the top so as to allow the top to move along a direction substantially parallel to a body axis of the subject; a control unit configured to controls the X-ray tube, the X-ray detector, the support unit, and the bed to scan the subject with X-rays while moving the top along the direction; an acquisition unit configured to acquires projection data via the X-ray detector; an extraction unit configured to extracts projection data necessary for reconstruction of image data associated with a predetermined slice position from the acquired projection data; a weighting unit configured to assigns a smaller weight to first projection data of the extracted projection data than a weight assigned to second projection data, the first projection data being acquired outside a predetermined period including a predetermined acquisition time of the projection data at the predetermined slice position, the second projection data being acquired within the predetermined period; and a reconstruction unit configured to reconstructs the image data on the basis of the first projection data and the second projection data to which the weights are assigned.

An X-ray CT apparatus according to a second aspect of the present invention comprises: an X-ray tube configured to generates X-rays; an X-ray detector configured to detects X-rays generated from the X-ray tube and transmitted through an subject placed on a top and includes a plurality of detector arrays formed by arranging a plurality of X-ray detection elements in a channel direction; a scan unit configured to scans the subject with X-rays while moving the top and rotating the X-ray tube and the X-ray detector while changing a speed of the top; an acquisition unit configured to acquires projection data via the X-ray detector; a weighting unit configured to assigns a weight to the projection data in accordance with a speed of the top at an acquisition time of the acquired projection data; and a reconstruction unit configured to reconstructs image data on the basis of the weighted projection data.

An X-ray CT apparatus according to a third aspect of the present invention comprises: an X-ray tube configured to generates X-rays; an X-ray detector configured to detects X-rays generated from the X-ray tube and transmitted through an subject placed on a top; a support unit configured to rotatably supports the X-ray tube and the X-ray detector; a bed configured to includes the top so as to allow the top to move along a direction substantially parallel to a body axis of the subject; a control unit configured to controls the X-ray tube, the X-ray detector, the support unit, and the bed to scan the subject with X-rays while moving the top along the direction; an acquisition unit configured to acquires projection data via the X-ray detector; a determination unit configured to determines whether the acquisition unit has acquired projection data corresponding to a necessary range for reconstruction of image data at a predetermined slice position; a weighting unit configured to assigns a predetermined value to data, of the projection data corresponding to the necessary range, which corresponds to a range in which no data has been acquired by the acquisition unit, when the determination unit determines that projection data corresponding to the necessary range has not been acquired, and assigns a weight larger than the predetermined value to projection data, of the necessary projection data, which corresponds to the range which has been acquired by the acquisition unit; and a reconstruction unit configured to reconstructs the image data on the basis of data assigned with the predetermined value and projection data assigned with the weight.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the preferred embodiments given below, serve to explain the principles of the invention.

FIG. 1 is a block diagram showing the arrangement of an X-ray CT apparatus according to an embodiment of the present invention;

FIG. 7 is a view showing the relationship between projection data, a one-dimensional weighting function, and the speed of a top in step S1 in FIG. 6;

FIG. 9 is a view showing a case in which a shift-invariant weighting function is applied to projection data at a position Z0 in FIG. 8;

DETAILED DESCRIPTION OF THE INVENTION

Figure 2:
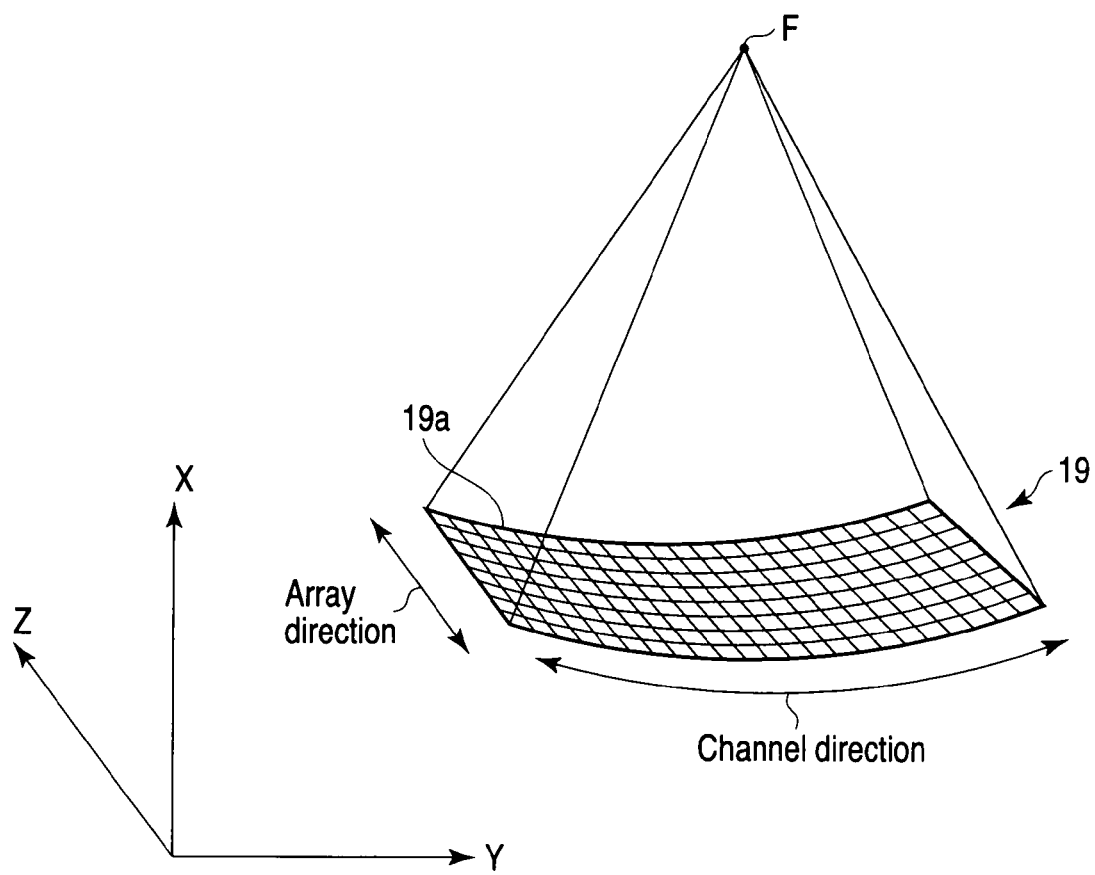
FIG. 2 is a view showing the structure of an X-ray detector in FIG. 1.

An X-ray computed tomography (CT) apparatus according to an embodiment of the present invention will be described below with reference to the views of the accompanying drawing. Note that X-ray CT apparatuses include various types of apparatus, e.g., a rotate/rotate apparatus in which an X-ray tube and X-ray detector rotate together around an subject, and a stationary/rotate apparatus in which many detection elements are arrayed in the form of a ring, and only an X-ray tube rotates around an subject. The present invention can be applied to either type. In this case, the rotate/rotate type will be exemplified. In order to reconstruct one-slice image data in the full scan method, projection data corresponding to one rotation around an subject, i.e., about $2\pi$, is required. In order to reconstruct one-slice image data in the half scan method, projection data corresponding to $\pi+\alpha$ [rad] ($\alpha$: fan angle) is required. This embodiment can be applied to either the full scan method or the half scan method. For a concrete description, this embodiment uses the half scan method.

FIG. 1 is a block diagram showing the arrangement of an X-ray CT apparatus 1 according to this embodiment. The X-ray CT apparatus 1 comprises a gantry device 10 and a computer device 30. The gantry device 10 rotatably supports an annular or disk-like rotating frame 11. The rotating frame 11 has an X-ray tube 17 and a multi-slice X-ray detector 19 which face each other through an subject P which is placed on a top 15 of a bed 13 in an imaging area. A gantry driving device 21 continuously rotates the rotating frame 11 at a constant angular velocity. In this case, the rotation axis of the rotating frame 11 is defined as a Z-axis, an axis which connects the focal point of the X-ray tube 17 to the center of the detection surface of the X-ray detector 19 and is perpendicular to the Z-axis is defined as an X-axis, and an axis perpendicular to the Z-axis and the X-axis is defined as a Y-axis. This X-Y-Z coordinate system is a rotational coordinate system with the Z-axis serving as a rotation axis. Assume that the subject P is placed on the top 15 such that the body axis of the subject almost matches the Z-axis.

The bed 13 includes the top 15 to allow it to slide along the Z-axis that is the direction substantially parallel to the body axis of the subject. The bed 13 has a driving motor for moving the top 15. The driving motor rotates in accordance with a driving signal from a scan control unit 31 to move the top 15 at a constant speed or variable speed within the period set by an input device 33 or the like. The driving motor of the bed 13 includes an optical or magnetic encoder 23. Every time the rotating shaft of the driving motor of the bed 13 rotates through a predetermined angle, the magnetic encoder 23 generates a pulse signal for detecting the rotational angle of the rotating shaft. The rotational angle of the rotating shaft corresponds to the Z-axial position of the top 15 (to be simply referred to as a top position hereinafter). The generated pulse signal is transmitted to the scan control unit 31 and a top information measurement unit 35.

The X-ray tube 17 generates cone beam X-rays upon receiving a high voltage and a filament current from a high voltage generator 25. As shown in FIG. 2, the X-ray detector 19 detects the cone beam X-rays generated from a focal point F of the X-ray tube 17. The X-ray detector 19 has a plurality of X-ray detection elements 19a which are densely distributed in both the channel direction (almost matching the Y-axis) and the array direction (Z-axis). A plurality of element arrays each having detection elements arrayed in a line along the channel direction are arranged side by side along the array direction (Z-axis). The spread angle of cone beam X-rays in the channel direction is called a fan angle, and the spread angle in the array direction is called a cone angle. Assume that the X-ray detector 19 has N channels and M arrays.

A data acquisition system (DAS) 27 is connected to the X-ray detector 19. The data acquisition system 27 converts a signal corresponding to the intensity of transmitted X-rays output from each channel of the X-ray detector 19 into a digital signal. This digital signal is called projection data. A set of projection data acquired by one-time generation of X-rays is called a view. A view angle indicates the rotational angle of the X-ray tube 17.

The computer device 30 includes the scan control unit 31 as a central unit, the input device 33, the top information measurement unit 35, a preprocessing unit 37, a projection data storage unit 39, a projection data extraction unit 41, a weighting unit 43, a reconstruction processing unit 45, an image data storage unit 47, an image processing unit 49, and an image display device 51.

The input device 33 inputs imaging conditions such as a slice position, the speed of the top, the size of an imaging area (FOV), a helical pitch (information associated with the moving speed of the top 15), an X-ray tube voltage, and a tube current. The scan control unit 31 controls the respective units to perform helical scanning on the basis of input imaging conditions.

The top information measurement unit 35 measures the position and speed of the top 15 on the basis of the pulse signals transmitted from the encoder 23.

The preprocessing unit 37 performs preprocessing such as sensitivity correction for the projection data output from the data acquisition system 27. The preprocessed projection data is temporarily stored in the projection data storage unit 39. The projection data storage unit 39 stores, in association with projection data, codes representing a view number representing an acquisition time (an order in acquisition), a view angle, a channel number, an array number, the position of the top 15, and the speed of the top 15.

The projection data extraction unit 41 extracts, from the projection data storage unit 39, projection data (actual data and opposed data) in a range necessary for the reconstruction of image data at the slice position designated by the input device 33, on the basis of information which can uniquely specify projection data. The range necessary for reconstruction is the angular range from $(-\pi/2-\alpha/2)$ to $(+\pi/2+\alpha/2)$, with the slice position being the center (0). A set of projection data (views) in the angular range of $\pi+\alpha$, centered on a slice position, will be called a projection data set. The number of views contained in a projection data set will be called View-Process. In addition, (ViewProcess/2) will be called a view center. Note that information which can uniquely specify projection data is at least one of pieces of information such as a view angle, a view number, and a top position which are associated with the projection data.

In order to weight and normalize the extracted projection data set, the weighting unit 43 multiplies the projection data set by a two-dimensional weighting function (to be referred to as a data redundancy correction function hereinafter) W[ch, view]. The weighting unit 43 then removes the projection data acquired via element arrays which do not contribute to reconstruction processing from the projection data contained in the projection data set weighted and normalized by using the contribution table, and outputs the projection data acquired via contributing element arrays.

The data redundancy correction function W[ch,view] is calculated for each ray of projection data set. The data redundancy correction function W[ch,view] is a two-dimensional function having a channel number and a view number as variables. The data redundancy correction function W[ch, view] has a weight distribution point-asymmetrical with respect to the channel center of a projection data set and line-asymmetrical to the view center.

The data redundancy correction function W[ch,view] is generated on the basis of a weighting function C[view]. The weighting function C[view] is a one-dimensional function having a view number as a variable. The weighting function C[view] has a weight distribution corresponding to the actual distances from a slice position to views. More specifically, the weighting function C[view] assigns smaller weights to views having longer actual distances from a slice position and larger weights to views having shorter actual distances from the slice position in accordance with changes in the speed of the top 15. The weighting function C[view] has a weight distribution line-asymmetrical to the view center of a projection data set. The weighting function C[view] is generated on the basis of the acquisition time of projection data at a slice position and the acquisition period of a projection data set used for reconstruction processing.

The contribution table changes in accordance with a slice position, the speed of the top 15, and the view range (View-Process) of projection data used for reconstruction processing.

The reconstruction processing unit 45 reconstructs image data by performing reconstruction processing for a projection data set from the weighting unit 43. Reconstruction processing comprises filtering processing, backprojection processing, and the like. Typically, a reconstruction method is cone beam reconstruction method. The cone beam reconstruction method is a method of performing backprojection processing upon determining projection data to be back-projected to reconstruction pixels in consideration of a cone angle. The reconstructed image data is stored in the image data storage unit 47, together with a code representing a slice position.

The image processing unit 49 performs various kinds of known image processing for reconstructed image data. The image display device 51 displays the image having undergone the image processing.

The X-ray CT apparatus 1 having the above arrangement accelerates the top 15 at a constant positive acceleration during helical scanning. The range in which the top 15 is accelerated is the range of at least $\pi+\alpha$, which includes a slice position, with reference to the slice position. Note that the top 15 is accelerated at a constant positive acceleration. However, this embodiment is not limited to this. This embodiment can be applied to any acceleration including negative acceleration. The operation of the X-ray CT apparatus 1 will be described below.

The weighting function C[view], the data redundancy correction function W[ch,view], and the contribution table which are characteristic to this embodiment will be described first. The weighting function C[view] has a weight distribution line-asymmetrical to the view center of a projection data set. The weighting function C[view] assigns smaller weights to projection data farther from a slice position and assigns larger weights to projection data at the slice position and projection data closer to the slice position.

Figure 3:
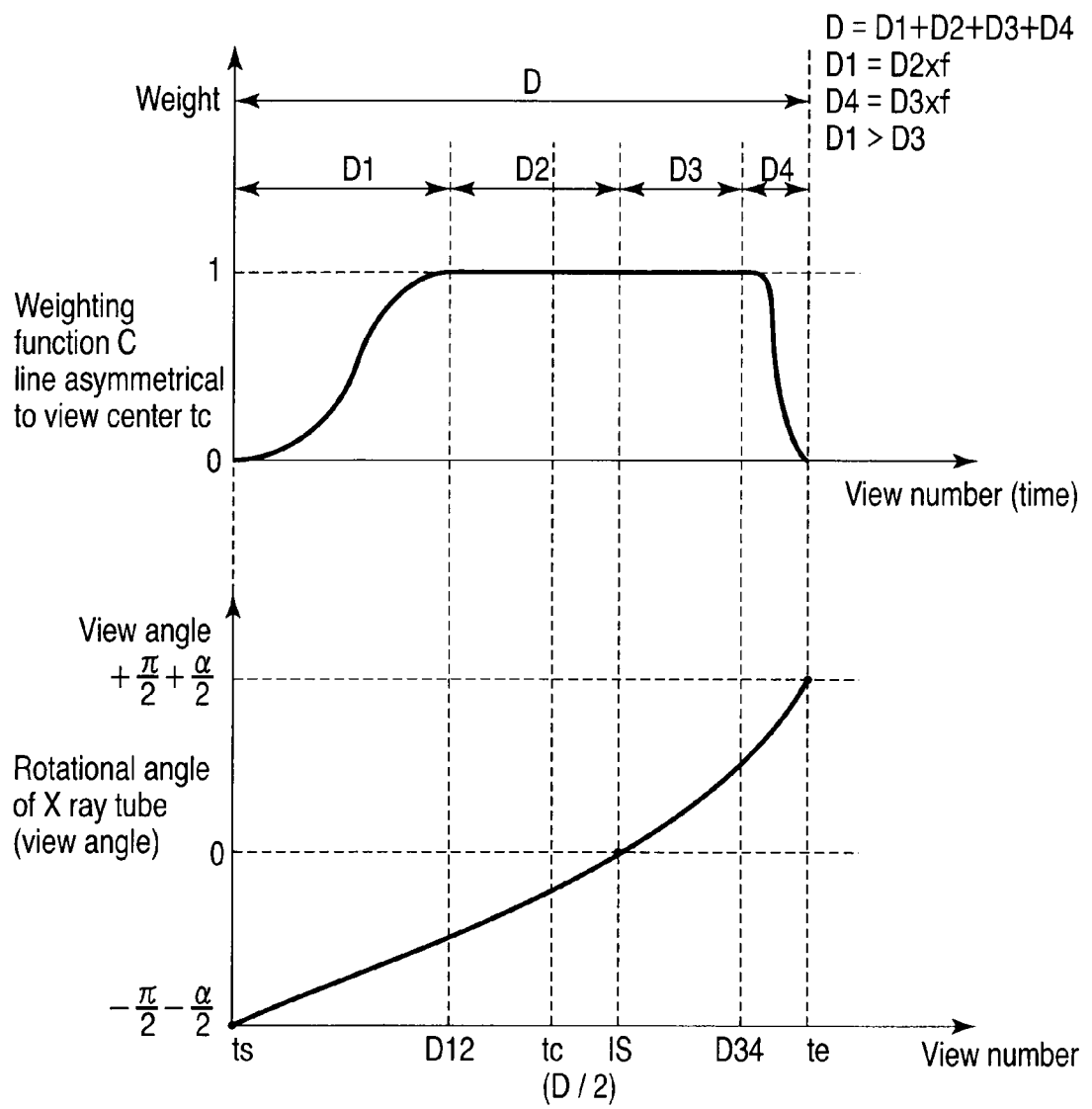
FIG. 3 is a graph showing the relationship between a one-dimensional weighting function and the rotational angle of an X-ray tube according to this embodiment.

FIG. 3 is a graph showing the weighting function C[view] and the rotational angle (view angle) of the X-ray tube 17. Let ts be a view number at the start position of reconstruction processing, and te be a view number at the end position of the reconstruction processing. That is, a range (the number of views) D from the view number ts to the view number te matches the acquisition period of a projection data set. The top 15 accelerates from the view number ts to the view number te. The number of views from the view number ts to the slice position IS is larger than that from a slice position tc to the view number te. The view center tc which is the middle of the view range D does not match the slice position IS at which reconstruction is performed. The mismatch between the slice position IS and the view center tc is caused by changes in the speed of the top 15 during helical scanning. As the speed of the top 15 increases, the view density decreases. That is, the view density from the view angle $(-\pi/2-\alpha/2)$ to the view angle (0) is higher than that from the view angle (0) to the view angle $(+\pi/2+\alpha/2)$.

A sequence in which the weighting unit 43 generates the weighting function C[view] will be described with reference to FIG. 3. When a projection data set is extracted, the weighting unit 43 determines a view range (D1+D2) between the view number ts at the start position of reconstruction processing and the slice position IS. The weighting unit 43 then determines a view range (D3+D4) is a view range between the slice position IS and the view number te at the end position of the reconstruction processing. The weighting unit 43 then calculates a midpoint D12 between the view number ts and the slice position IS. The weighting unit 43 then calculates a midpoint D34 between the slice position IS and the view number te.

A view range D1 from the view number ts to the midpoint D12 and a view range D2 from the midpoint D12 to the slice position IS are set to D1=D2×f. In addition, a range D3 from the slice position IS to the midpoint D34 and a range D4 from the midpoint D34 to the view number te are set according to D4=D3×f. The factor f determines the proportions of the view ranges D1, D2, D3, and D4 occupying the view range D. The operator can arbitrarily set the value of the factor f through the input device 33. Since the top 15 is accelerated, D1>D3. The ranges D2 and D3 are set to the weight "1". Weights from the view number ts to the midpoint D12 are determined by an S-shaped cubic curve connecting the value "0" to the value "1". In addition, weights from the midpoint D34 to the view number te are determined by an inverted S-shaped cubic curve connecting the value "1" to the value "0". Assume that the weight at the midpoint of the cubic curve view range is "0.5". However, curves in the ranges D1 and D4 are not limited to cubic curves, and can be linear or quadratic curves depending on how the speed of the top 15 changes.

If, for example, the speed of the top 15 is high, projection data near the end of a projection data set in the view direction is spaced too far from the slice position. This causes artifacts. For this reason, the weight assigned to projection data having a predetermined distance or more from the slice position is preferably set to "0". The distance from the slice position can be calculated from the distance between the slice position and the position of the top 15 associated with the projection data.

In this manner, the weighting function C[view] assigns the weight "1" to projection data, of the projection data contained in a projection data set, which is included in the view range (D2 and d3) of a predetermined number of views from the slice position IS. On the other hand, the weighting function C[view] assigns a weight smaller than "1" to projection data, of the projection data contained in the projection data set, which is included in the range (D1 and D4) spaced apart from the slice position IS by a predetermined number of views. That is, the weighting function C[view] assigns the weight "1" to a view located within a predetermined actual distance from the slice position IS, and assigns a weight smaller than "1" to a view located outside the predetermined actual distance from the slice position IS, regardless of the speed of the top 15. Securing a predetermined amount of projection data to be assigned with the weight "1" can prevent the occurrence of artifacts due to a shortage of projection data assigned with the weight "1". The ratio between the number of views assigned with the weight "1" and the number of views assigned with weights other than "1", i.e., the value of a predetermined actual distance, can be arbitrarily set by the weighting unit 43. More specifically, the weighting unit 43 sets the ratio between the number of views assigned with the weight "1" and the number of views assigned with weights other than "1" on the basis of the value of the factor f input via the input device 33. Note that the factor f is preferably set to make the view range D1 become about 30% or less of the view range D, from the viewpoint of the prevention of artifacts due to a shortage of data.

The weighting function C[view] set by the above sequence is not a function line-symmetrical to the view center like the conventional shift-invariant weighting function, but is a function line-asymmetrical to the view center. A function line-asymmetrical to the view center will be called a shift-variant weighting function. Using the shift-variant weighting function C[view] can assign proper weights to the projection data acquired by variable speed helical scanning in accordance with changes in the speed of the top 15.

The data redundancy correction function W[ch,view] calculated by the weighting unit 43 on the basis of the shift-variant weighting function C[view] will be described next. The value of the data redundancy correction function W[ch, view] is calculated for each ray of a projection data set before reconstruction processing. The value of the data redundancy correction function W[ch,view] is calculated on the basis of mathematical expressions 1 to 7.

$$\Delta \gamma = \frac{FanAngle}{Nch} \quad (1)$$

$$\Delta \beta = \frac{2\pi}{ViewRev} \quad (2)$$

$$\gamma[ch] = (ch - Cch) \times \Delta \gamma \quad (3)$$

$$\beta[view] = view \times \Delta \beta \quad (4)$$

$$Nrot = (ceil)\frac{ViewProcess}{ViewRev} \quad (5)$$

$$tmpReal[view] = \sum_{n=-Nrot}^{Nrot} C\left[view + 2.0 \times n \times \frac{viewRev}{2.0}\right] \quad (6)$$

$$tmpTaiko[ch, view] = \sum_{n=-Nrot}^{Nrot} C\left[view + 2 \times n \times \frac{viewRev}{2.0} \times \frac{2.0 \times \gamma[ch]}{\Delta \beta}\right] \quad (7)$$

$$W[ch, view] = \frac{C[ch, view]}{tmpReal[view] + tmpTaiko[ch, view]} \quad (8)$$

The following parameters are used in mathematical expressions 1 to 7:
FanAngle: fan angle of X-rays (constant)
Nch: number of channels of X-ray detector (constant)
Δγ: fan angle between adjacent channels (constant)
ViewRev: number of views acquired during one revolution of X-ray tube (constant)
Δβ: rotational angle of X-ray tube between adjacent views (constant)
ch: channel number of projection data (constant)
Cch: central channel number of X-ray detector (constant)
γ[ch]: fan angle of ch (function of ch)
View: a view number (variable)
ceil: rounding up all digits to right of decimal point
Viewprocess: number of views of a projection data set necessary for reconstruction of one image (constant)
C: shift-variant weighting function C (function of view)
tmpReal[view]: total sum of weighting functions C by which all actual rays of a projection data set are multiplied (function of view)
tmpTaiko[ch,view]: total sum of weighting functions C by which all opposed rays of projection data set are multiplied (function of view)
W[ch,view]: data redundancy correction function W (function between ch and view).

An example of a concrete sequence in which the weighting unit 43 calculates the data redundancy correction function W[ch,view] and normalizes projection data will be described. Calculation processing for the data redundancy correction function W[ch,view] is performed for each ray of a projection data set. First of all, the weighting unit 43 calculates Δγ, Δβ, γ, and Nrot for each ray according to mathematical expressions 1, 2, 3, and 4 on the basis of imaging conditions and the like. The weighting unit 43 then calculates tmpReal[ch,view] and tmpTaiko[ch,view] according to mathematical expressions 5 and 6. The weighting unit 43 calculates the value of the data redundancy correction function W[ch,view] according to mathematical expression 7. In this sequence, the weighting unit 43 calculates the data redundancy correction function W[ch,view] for each of all the rays, and normalizes all projection data sets.

As described above, the data redundancy correction function W[ch,view] is determined on the basis of the weighting function C[view]. The data redundancy correction function W[ch,view] is a two-dimensional function line-asymmetrical to the view center and point-asymmetrical with respect to the central channel. Asymmetry with respect to the view direction and the channel direction makes it possible to properly normalize projection data in accordance with changes in the speed of the top 15. In variable speed helical scanning, therefore, artifacts due to the mismatch between a slice position and the view center of a projection data set are reduced. As a result, the image quality of reconstruction image data improves.

A contribution table will be described next. The weighting unit 43 determines a contribution table on the basis of a slice position and the position of the top 15. The weighting unit 43 removes projection data, of the normalized projection data set, which correspond to arrays which do not contribute to reconstruction processing.

Figure 4:
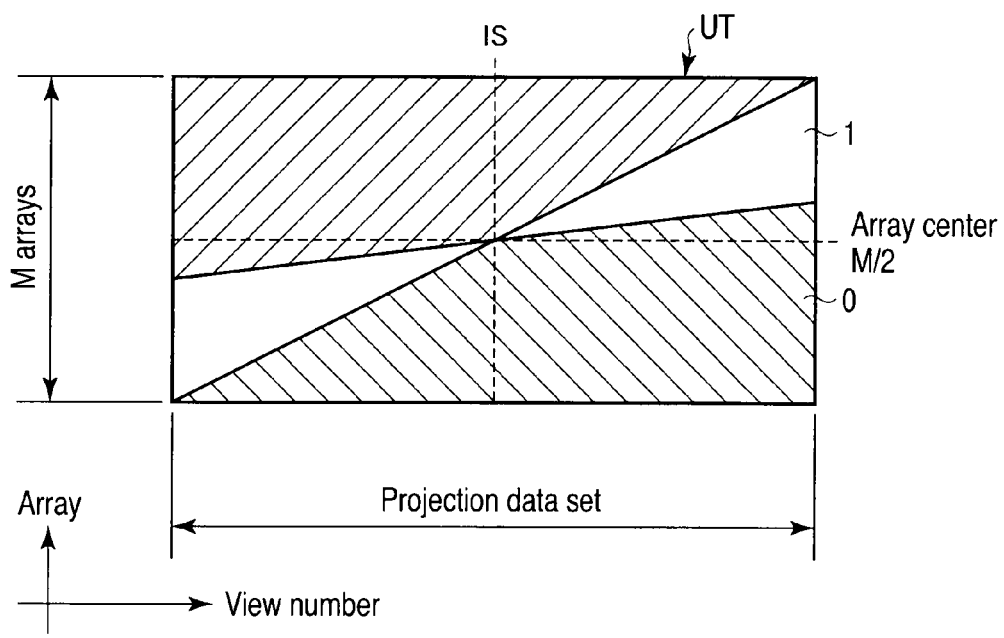
FIG. 4 is a view showing a contribution table in constant speed helical scanning.

FIG. 4 is a view showing an example of a contribution table UT in constant speed helical scanning. The rightward direction indicates view numbers, and the longitudinal direction indicates the array numbers of projection data. Projection data within the range of the contribution "1" are not removed, and projection data within the range of the contribution "0" are removed. The contribution of an array is determined in accordance with a view angle (or a view number) from a slice position, and linearly shifts to the center of the array while the contribution width in the array direction is reduced from the end of view numbers to the image center. In the case of constant speed helical scanning, the contribution of an array is point-symmetrical with respect to the intersection of an array center M/2 and the slice position IS.

Figure 5:
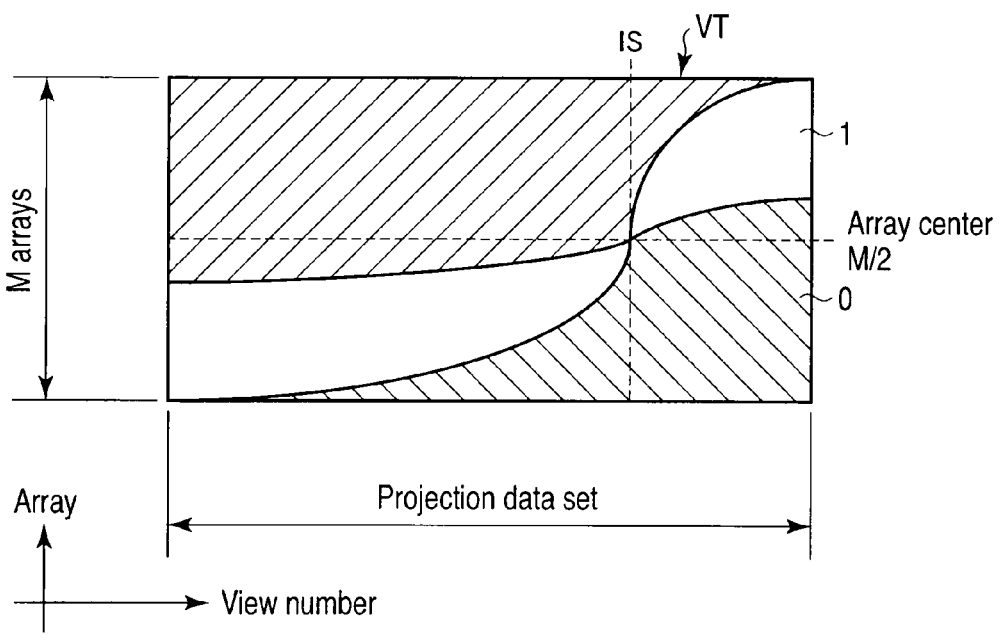
FIG. 5 is a view showing a contribution table in variable speed helical scanning according to this embodiment.

FIG. 5 is a view showing an example of a contribution table VT in variable speed helical scanning. As described above, the contribution of an array is determined in accordance with a view angle (or a view number) from a slice position. Therefore, the contribution of an array at a given view number does not change in constant speed helical scanning and variable speed helical scanning. In other words, the contribution of an array in the contribution table UT in constant speed helical scanning is equal to that of an array at the same view in the contribution table VT in variable speed helical scanning. Therefore, the range of the contribution "1" of arrays in a case in which the speed of the top is accelerated has a distorted shape, as shown in FIG. 5. Applying the contribution table VT to a projection data set can properly remove projection data corresponding to arrays which do not contribute to reconstruction processing even when the speed of the top 15 changes. As a consequence, artifacts in reconstructed image data are reduced to improve the image quality. Note that the contribution table VT described above is an example, and another contribution table can be used. For example, the contributions of the table may change in several steps or continuously between "0" and "1" instead of changing in only two steps between "0" and "1".

The weighting function C[view], the data redundancy correction function W[ch,view], and the contribution table VT are changed every time the above parameter, the slice position, the speed of the top 15, and the like are changed.

Figure 6:
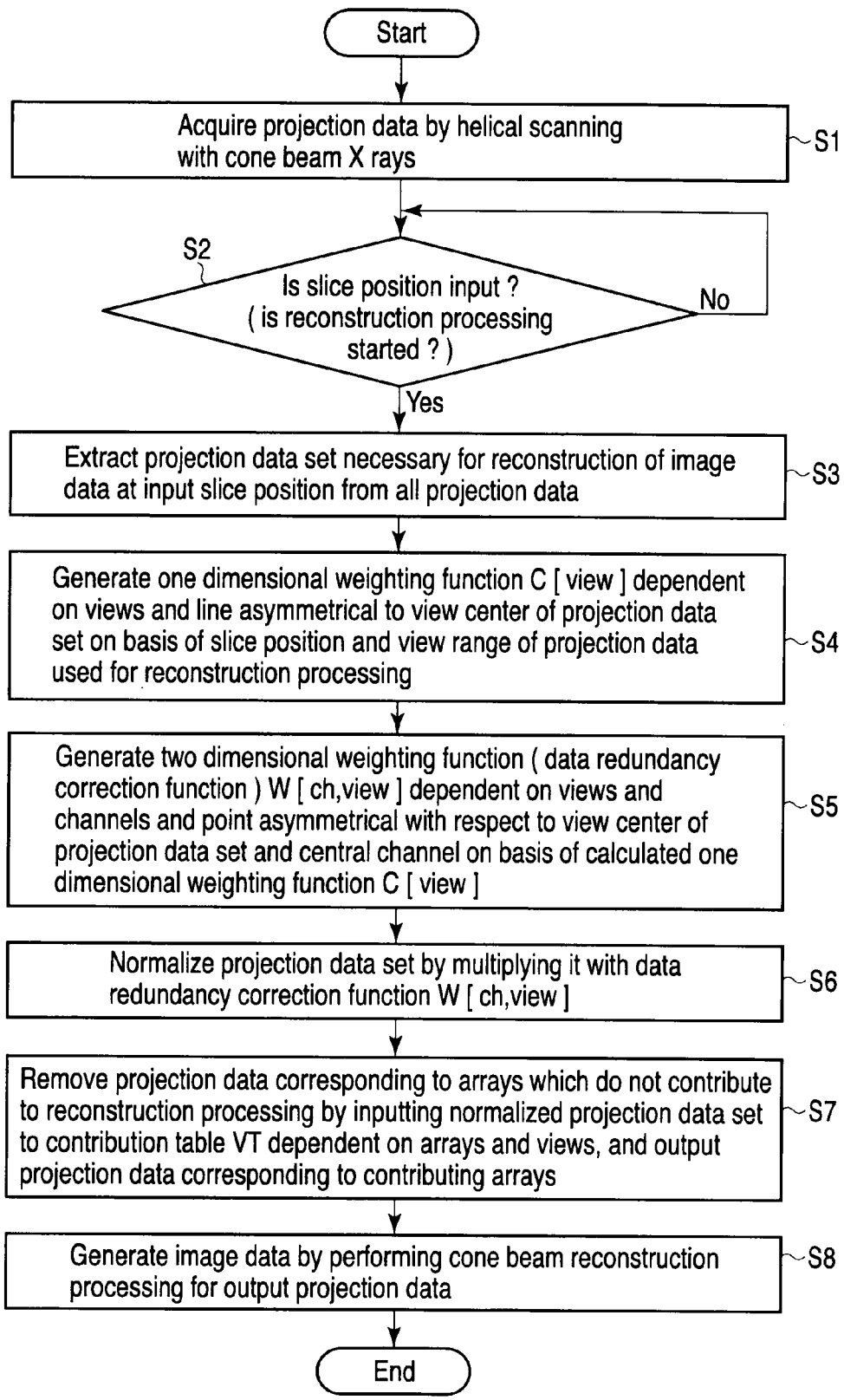
FIG. 6 is a flowchart showing a processing sequence from the start of helical scanning to the reconstruction of image data in this embodiment.

A sequence from the start of helical scanning using the data redundancy correction function W and the contribution table VT described above to the generation of image data under the control of the scan control unit 31 will be described next. FIG. 6 is a flowchart showing a sequence from the start of helical scanning to the generation of image data. FIG. 7 is a view showing the relationship between projection data and the weighting function C[view].

First of all, the scan control unit 31 helically scans an subject with cone beam X-rays by controlling the respective constituent elements of the X-ray CT apparatus 1 (step S1). The projection data storage unit 39 stores the projection data acquired by helical scanning. When the projection data is stored, the scan control unit 31 waits ready to designate a slice position (issue an instruction to start reconstruction processing) (step S2). Upon receiving a code representing a slice position from the operator via the input device 33 (YES in step S2), the scan control unit 31 causes the projection data extraction unit 41 to perform projection data extraction processing (step S3). In projection data extraction processing, the projection data extraction unit 41 extracts a projection data set in the angular range from $(-\pi/2-\alpha/2)$ to $(+\pi/2+\alpha/2)$ on the two sides of the input slice position from all the stored projection data.

When a projection data set is extracted, the scan control unit 31 causes the weighting unit 43 to perform weighting function calculation processing. In weighting function calculation processing, the weighting unit 43 calculates the shift-variant weighting function C[view] dependent on views on the basis of a slice position and a top position stored in association with projection data (step S4). The weighting unit 43 then calculates the data redundancy correction function W[ch,view] according to mathematical expressions 1 to 7 (step S5). Upon calculating the data redundancy correction function W[ch,view], the weighting unit 43 normalizes the projection data set by multiplying the projection data set by the data redundancy correction function W[ch,view] (step S6). The processing in steps S5 and S6 is performed for each ray of the projection data set. Upon completing normalization for all the rays, the weighting unit 43 applies the contribution table in variable speed helical scanning to the normalized projection data set to remove projection data of the projection data set. The removed projection data correspond to arrays which do not contribute to reconstruction processing. As a consequence, projection data corresponding to contributing arrays are output (step S7). In step S7, the weighting processing is terminated.

When the weighting processing is terminated, the scan control unit 31 causes the reconstruction processing unit 45 to perform reconstruction processing (step S8). In reconstruction processing, the reconstruction processing unit 45 generates image data at the input slice position by performing cone beam reconstruction processing for the projection data set output in step S7.

According to this embodiment, in variable speed helical scanning in which the slice position of the image to be reconstructed does not match the center of the projection data set, the X-ray CT apparatus 1 calculates the data redundancy correction function W[ch,view] asymmetrical to a slice position and the view center of projection data on the basis of the slice position and the top position. The X-ray CT apparatus 1 multiplies the projection data set by the calculated data redundancy correction function W[ch,view]. The X-ray CT apparatus 1 removes projection data corresponding to arrays which do not contribute to reconstruction processing by applying the contribution table VT to the projection data set, and outputs projection data corresponding to contributing arrays. The X-ray CT apparatus 1 then reconstructs image data on the basis of the output projection data. According to this embodiment, therefore, it is possible to reduce artifacts due to the mismatch between a slice position and the view center of a projection data set in variable speed helical scanning.

(Modification)

A modification of this embodiment will be described below. Note that in the following description, the same reference numbers denote constituent elements having almost the same functions, and a repetitive description will be made only when required. A so-called "outrange view" problem is known in constant speed helical scanning. When "outrange view" occurs, a slice position does not match the view center of a projection data set. The X-ray CT apparatus 1 according to the modification solves this "outrange view" problem by using the data redundancy correction function W[ch,view] described above. The "outrange view" problem will be described first.

Figure 8:
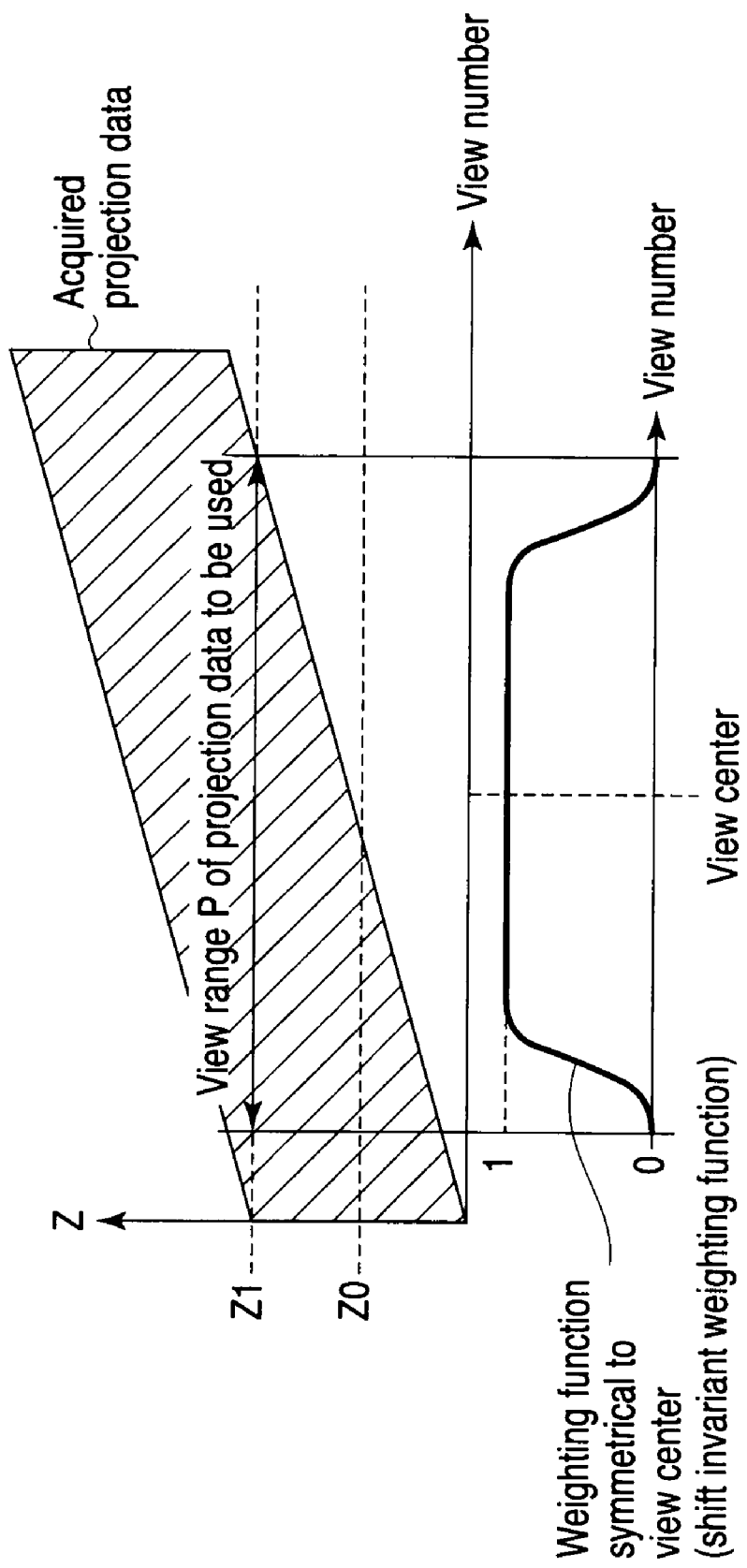
FIG. 8 is a view showing the view range of projection data acquired by constant speed helical scanning and the range of projection data used for reconstruction processing in the array direction (Z-axis) according to a modification of this embodiment.

FIG. 8 is a view showing the view range of projection data acquired by constant speed helical scanning and the range of projection data used for reconstruction processing in the array direction (Z-axis). Assume that, as shown in FIG. 8, projection data have been acquired by helically scanning a given imaging area. The range of the acquired projection data shifts in the Z-direction at a constant rate with the lapse of time (view number). In reconstruction processing, first of all, the projection data extraction unit 41 extracts projection data corresponding to a view range P (ViewProcess) used for reconstruction processing. When image data at a position Z1 is to be reconstructed, since projection data corresponding to the view range P has been acquired, reconstruction processing is performed without any problem. The weighting function used in this case is a shift-invariant weighting function having a weight distribution symmetrical to the view center as in a normal case.

In some case, image data at a position Z0 near the start position of scanning is reconstructed. At position Z0, however, projection data corresponding to the view range P used for reconstruction processing have not been acquired. In this case, as shown in FIG. 9, when a general shift-invariant weighting function is used, a weight is applied to even nonexistent projection data. As a result, severe artifacts are generated in the reconstructed image data. Therefore, in order to guarantee the reconstruction of image data at position Z0, an imaging area is set to be wider than a reconstruction area. That is, acquiring projection data by helically scanning an area outside the reconstruction area in advance can reconstruct image data at position Z0. This is the "outrange view" problem.

In order to solve the "outrange view" problem, therefore, the X-ray CT apparatus 1 according to the modification of this embodiment uses the shift-variant weighting function C[view] having a weight distribution asymmetrical to the view center. First of all, when a slice position is input through the input device 33 or the like, the projection data extraction unit 41 extracts a projection data set necessary for the reconstruction of image data associated with the input slice position. In this case, the projection data extraction unit 41 determines whether there is projection data corresponding to the view range (length) P (ViewProcess) necessary for reconstruction processing.

Figure 10:
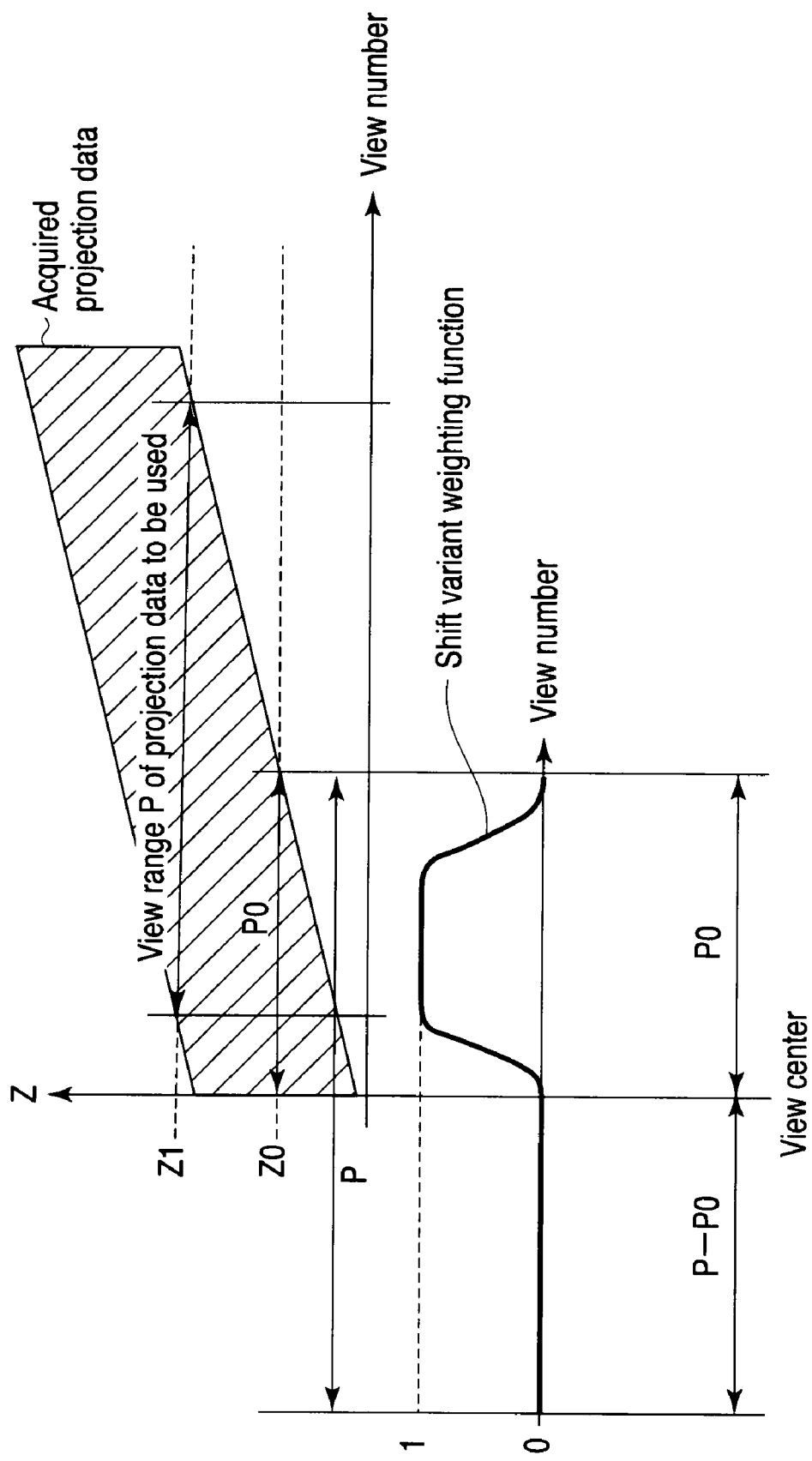
FIG. 10 is a view showing a case in which a shift-variant weighting function is applied to the projection data at position Z0 in FIG. 8.
Figure 11:
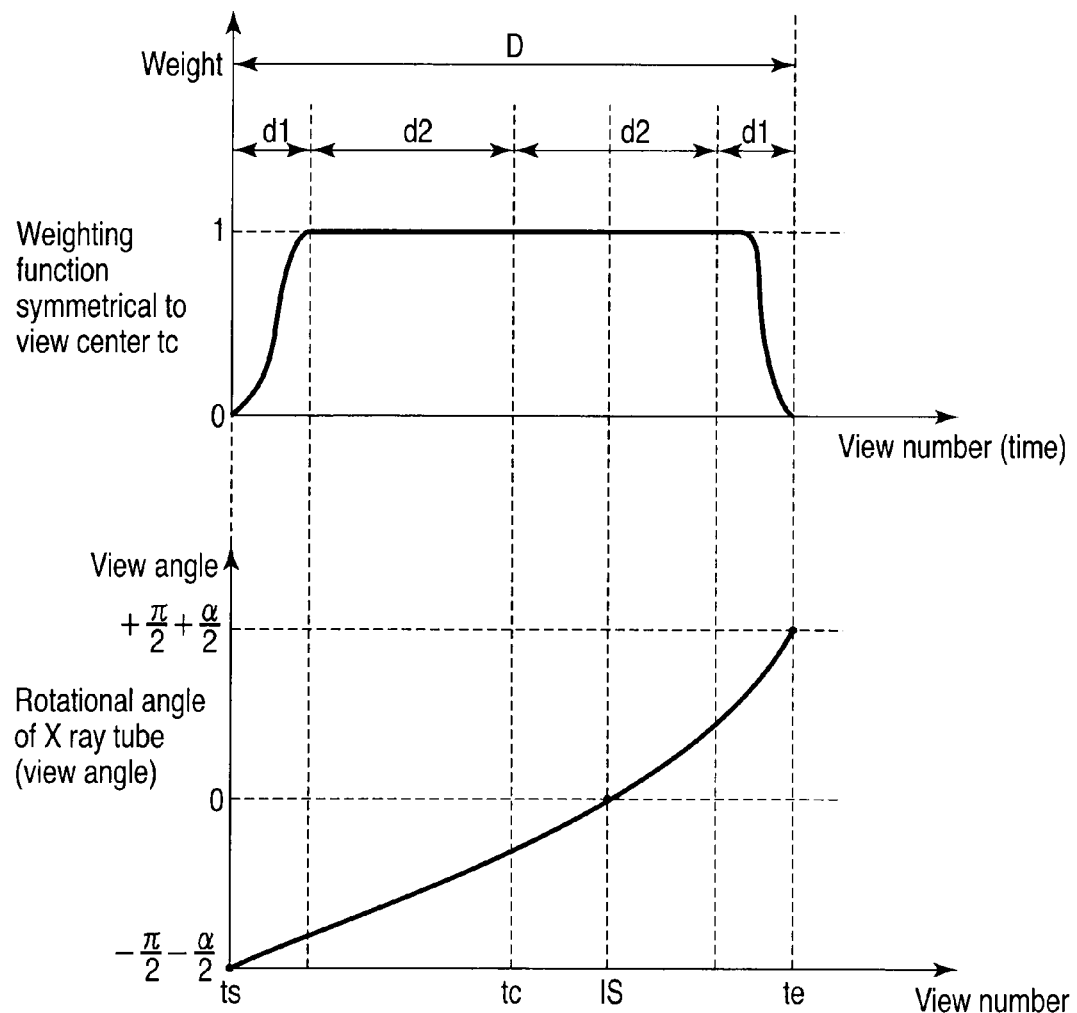
FIG. 11 is a view showing the relationship between a one-dimensional weighting function symmetrical to the view center and the rotational angle of an X-ray tube.

The shift-variant weighting function C[view] to be used by the weighting unit 43 when it is determined that there is no such projection data will be described below. FIG. 10 is a view showing the weighting function C[view] to be used when there is no projection data corresponding to the view range P. Assume that, as shown in FIG. 10, projection data corresponding to a view range P of the view range P0 has been acquired, and projection data corresponding to a view range P−P0 of the view range P has not been acquired. The weighting unit 43 sets the weight of the weighting function C[view] in the view range P−P0 to "0". That is, the value "0" is assigned to data corresponding to the view range P−P0. On the other hand, the weighting unit 43 changes the weight of the weighting function C[view] in the view range P0 in accordance with the view number. For example, the weights set in the range P0 have a weight distribution similar to that of a shift-invariant weighting function [view], as shown in FIG. 10. It suffices to set another weighting function such that the weights in the view range P0 gradually increase from the end array to the intermediate array. For the sake of simplicity, assume that the length of the view range P0 is equal to that of the view range P−P0. However, the modification of this embodiment is not limited to this, and it suffices that P0≠(P−P0).

When the shift-variant weighting function C[view] is set, the weighting unit 43 calculates the data redundancy correction function W[ch,view] on the basis of the weighting function C[view]. The weighting unit 43 normalizes a projection data set by applying the data redundancy correction function W[ch,view] to the projection data set. The weighting unit 43 then removes the projection data acquired by arrays which do not contribute to reconstruction processing by applying the contribution table UT in constant speed helical scanning to the normalized projection data set. The reconstruction processing unit 45 generates image data by performing reconstruction processing for the projection data left unremoved.

If it is determined that the projection data extraction unit 41 has extracted projection data corresponding to the view range P which is necessary and sufficient for reconstruction processing, as described in this embodiment, the weighting unit 43 performs weighting, and the reconstruction processing unit 45 performs reconstruction processing, thereby reconstructing image data at the input slice position.

As in the above arrangement, in the modification of this embodiment, when an image is to be reconstructed at a position where there is not projection data corresponding to a range which is used for reconstruction processing, a weighting function having a weight distribution asymmetrical to the view center is used to set the weight "0" in the range in which projection data does not exist. According to the modification of this embodiment, it is possible to solve the "outrange view" problem by using the weighting function C[view] having a weight distribution asymmetrical to the view center.

Note that this embodiment can be applied to fan beam X-rays as well as cone beam X-rays. In this case, the weighting function C[view] and the data redundancy correction function W[ch,view] are applied to a projection data set, but the contribution tables VT and UT are not applied.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X ray computed tomography apparatus comprising:
an X ray tube configured to generate X rays;
an X ray detector configured to detect X rays generated from the X ray tube and transmitted through a subject placed on a top;
a support unit configured to rotatably support the X ray tube and the X ray detector;

a bed configured to include the top so as to allow the top to move along a direction substantially parallel to a body axis of the subject;

a control unit configured to control the X ray tube, the X ray detector, the support unit, and the bed to scan the subject with X rays while moving the top along the direction and changing a speed of the top;

an acquisition unit configured to acquire projection data via the X ray detector;

an extraction unit configured to extract projection data necessary for reconstruction of image data associated with a predetermined slice position from the acquired projection data;

a weighting unit configured to apply a weighting function to the extracted projection data, the weighting function being determined in accordance with the speed of the top during the scan of the subject, the extracted projection data including first projection data and second projection data, the first projection data being acquired within a predetermined period including a predetermined time at which projection data is acquired at the predetermined slice position, the second projection data being acquired outside the predetermined period, the weighting function having a weight distribution which applies a smaller weight to the second projection data than to the first projection data; and a reconstruction unit configured to reconstruct the image data on the basis of the first projection data and the second projection data to which the weights are assigned.

2. The apparatus according to claim 1, wherein the weighting unit is configured to reduce a value of the weight assigned to each projection data included in the first projection data in accordance with a time difference from the predetermined acquisition time.

3. The apparatus according to claim 1, wherein the weighting unit is configured to assign the weights to the first projection data and the second projection data in accordance with actual distances from the slice position.

4. The apparatus according to claim 1, wherein the weighting unit is configured to assign weights to the first projection data and the second projection data by using a two-dimensional weighting function having a weight distribution which is asymmetrical to a center of a view of the extracted projection data and is asymmetrical with respect to a central channel.

5. The apparatus according to claim 4, wherein the weighting unit is configured to generate a one-dimensional weighting function having a weight distribution asymmetrical with respect to the center of the view of the extracted projection data and the two-dimensional weighting function on the basis of a total sum of weights based on the one-dimensional weighting function with respect to all actual data and opposed data included in the extracted projection data.

6. The apparatus according to claim 5, wherein the weighting function is configured to determine the one-dimensional weighting function on the basis of the predetermined acquisition time and an acquisition period for the extracted projection data.

7. The apparatus according to claim 5, wherein the one dimensional weighting function has a weight distribution which changes in accordance with an actual distance from the predetermined slice position.

8. The apparatus according to claim 1, wherein
the extraction unit is configured to determine whether the acquisition unit has acquired the second projection data, and
the reconstruction unit is configured to reconstruct the image data on the basis of predetermined values corresponding to the second projection data and the first projection data when it is determined that the extraction unit has not acquired the second projection data.

9. The apparatus according to claim 1, wherein the weighting unit is configured to set the predetermined period on the basis of an input from an operator.

10. An X ray computed tomography apparatus, comprising:

an X ray tube configured to generate X rays;

an X ray detector configured to detect X rays generated from the X ray tube and transmitted through a subject placed on a top, the X-ray detector including a plurality of detector arrays formed by arranging a plurality of X ray detection elements in a channel direction;

a scan unit configured to scan the subject with X rays while moving the top and rotating the X ray tube and the X ray detector while changing a speed of the top;

an acquisition unit configured to acquire projection data via the X ray detector;

a weighting unit configured to assign a weight to the acquired projection data in accordance with a change in the speed of the top at an acquisition time of the acquired projection data; and a reconstruction unit configured to reconstruct image data on the basis of the weighted projection data.

11. An X ray computed tomography apparatus, comprising:

an X ray tube configured to generate X rays;

an X ray detector configured to detect X rays generated from the X ray tube and transmitted through a subject placed on a top;

a support unit configured to rotatably support the X ray tube and the X ray detector;

a bed configured to include the top so as to allow the top to move along a direction substantially parallel to a body axis of the subject;

a control unit configured to control the X ray tube, the X ray detector, the support unit, and the bed to scan the subject with X rays while moving the top along the direction;

an acquisition unit configured to acquire projection data via the X ray detector;

a determination unit configured to determine whether the acquisition unit has acquired projection data corresponding to a necessary range for reconstruction of image data at a predetermined slice position;

a weighting unit configured to assign a predetermined value to data, of the projection data corresponding to the necessary range, which corresponds to a range in which no data has been acquired by the acquisition unit, when the determination unit determines that projection data corresponding to the necessary range has not been acquired, and to assign a weight larger than the predetermined value to projection data, of the necessary projection data, which corresponds to the range which has been acquired by the acquisition unit; and a reconstruction unit configured to reconstruct the image data on the basis of data assigned with the predetermined value and projection data assigned with the weight.

* * * * *